United States Patent
Breyfogle et al.

(10) Patent No.: US 11,471,389 B2
(45) Date of Patent: Oct. 18, 2022

(54) ENHANCED STABILITY OF ZINC PYRITHIONE IN OXIDATIVE ENVIRONMENTS, SUCH AS SCALP SEBACEOUS FLUID

(71) Applicant: The Procter & Gamble Company, Cincinnati, OH (US)

(72) Inventors: Laurie Ellen Breyfogle, Milford, OH (US); Daniel Lawrence Custer, West Chester, OH (US); John David Carter, Mason, OH (US); Florencio Zaragoza Dörwald, Buochs (CH); Jody Laurel Jourden, Atlanta, GA (US)

(73) Assignee: The Procter & Gamble Company, Cincinnati, OH (US)

( * ) Notice: Subject to any disclaimer, the term of this patent is extended or adjusted under 35 U.S.C. 154(b) by 88 days.

(21) Appl. No.: 16/913,172

(22) Filed: Jun. 26, 2020

(65) Prior Publication Data

US 2020/0405600 A1    Dec. 31, 2020

Related U.S. Application Data

(60) Provisional application No. 62/868,133, filed on Jun. 28, 2019.

(51) Int. Cl.

| A61K 8/27 | (2006.01) |
|---|---|
| A61K 8/25 | (2006.01) |
| A61K 8/49 | (2006.01) |
| A61Q 5/00 | (2006.01) |
| A61Q 5/12 | (2006.01) |

(52) U.S. Cl.
CPC .............. *A61K 8/27* (2013.01); *A61K 8/25* (2013.01); *A61K 8/4933* (2013.01); A61K 2800/10 (2013.01); A61K 2800/5426 (2013.01); *A61Q 5/006* (2013.01); *A61Q 5/12* (2013.01)

(58) Field of Classification Search
CPC .......... A61K 8/27; A61K 8/25; A61K 8/4933; A61K 2800/10; A61K 2800/5426; A61Q 5/006; A61Q 5/12
See application file for complete search history.

(56) References Cited

U.S. PATENT DOCUMENTS

| 4,096,240 A | 6/1978 | Mathur | |
|---|---|---|---|
| 5,401,770 A * | 3/1995 | Taguchi | A61K 8/44 556/133 |

(Continued)

FOREIGN PATENT DOCUMENTS

| DE | 202013004905 U1 | 12/2013 |
|---|---|---|
| WO | 2018033328 A1 | 2/2018 |
| WO | 2018197118 A1 | 11/2018 |

OTHER PUBLICATIONS

Yanara Jeria et al., "Photochemically induced fluorescence coupled to second—Order multivariate calibration as analytical tool for determining imidacloprid in honeybees", Chemometrics and Intelligent Laboratory Systems 1602017) pp. 1-7.
All Office Actions, U.S. Appl. No. 16/388,032.
Amy M. Holmes et al: "Imaging the penetration and distribution of zinc and zinc species after topical application of zincpyrithione to human skin", Toxicology and Applied Pharmacology, vol. 343, Mar. 1, 2018, pp. 40-47.

(Continued)

*Primary Examiner* — Snigdha Maewall
(74) *Attorney, Agent, or Firm* — Linda M. Sivik

(57) ABSTRACT

The present invention discloses a personal care composition comprising:
(a) A polyvalent metal salt of pyrithione;
(b) A metal complex selected from the group consisting of:

COMPOUND I

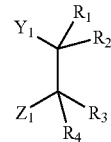

COMPOUND II

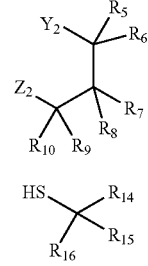

COMPOUND III
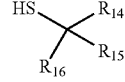

wherein $Y_1$, $Y_2$, $Z_1$, $Z_2$ are selected from the following groups: —$NH_2$, —$NHR_{11}$, —$NR_{12}R_{12}$, —NHCO—$R_{20}$, —SH, —$OR_{13}$, —O(C=O)—, phosphate.
and wherein at least one of $Y_1$ and $Z_1$ of compound I is —SH,
and wherein at least one of $Y_2$ and $Z_2$ of compound II is —SH
$R_1$, $R_2$, $R_3$, $R_4$, $R_5$, $R_6$, $R_7$, $R_8$, $R_9$, $R_{10}$, can independently be H, alkyl, substituted alkyl, phenyl, aryl;
$R_{14}$ is —$NH_2$, —NHCO—$CH_3$, —$NHR_{17}$, or —$NR_{18}R_{18}$
$R_{15}$ is —COOH, —$COOR_{19}$
$R_{11}$, $R_{12}$, $R_{13}$ $R_{16}$, $R_{17}$, $R_{18}$, $R_{19}$ can be independently be alkyl, substituted alkyl, phenyl, aryl.
and wherein the metal of the complex is selected from the group consisting of zinc, copper, and iron.

18 Claims, No Drawings

(56) References Cited

U.S. PATENT DOCUMENTS

| | | | |
|---|---|---|---|
| 5,723,112 A | 3/1998 | Bowser et al. | |
| 8,491,877 B2* | 7/2013 | Schwartz | A61K 8/27 504/272 |
| 10,837,908 B2 | 11/2020 | Stofel et al. | |
| 2002/0086039 A1 | 7/2002 | Lee et al. | |
| 2004/0213751 A1 | 10/2004 | Schwartz | |
| 2005/0151094 A1 | 7/2005 | Kitagawa | |
| 2010/0139682 A1 | 6/2010 | Edgar et al. | |
| 2013/0284195 A1 | 10/2013 | Murdock et al. | |
| 2016/0077077 A1 | 3/2016 | Shi et al. | |
| 2017/0209033 A1 | 7/2017 | Yu et al. | |
| 2018/0321139 A1 | 11/2018 | Helfmann et al. | |
| 2021/0106231 A1 | 4/2021 | Radhakrishnan et al. | |

OTHER PUBLICATIONS

Chen Guoqiang et al.: "Sensitive and simultaneous quantification of zinc pyrithione and climbazole deposition fromanti-dandruff shampoos onto human scalp", Journal of Chromatography B: Biomedical Sciences & Applications,Elsevier, Amsterdam, NL, vol. 1003, Sep. 11, 2015, pp. 22-26.

Javier Lopez Flores et al., "Determination of azoxystrobin residues in grapes, musts and wines with a multicommutedflow-through optosensor implemented with photochemically induced fluorescence", Science Direct, Analytica ChimicaActa 585 (2007) pp. 185-191.

Natalie L. Garrett et al.: "Imaging microscopic distribution of antifungal agents in dandruff treatments with stimulatedRaman scattering microscopy", Journal of Biomedical Optics, vol. 22, No. 6, Jun. 9, 2017, p. 066003.

PCT Search Report and Written Opinion for PCT/US2020/070193 dated Oct. 6, 2020, 9 pages.

World Health Organization: International Agency for Research on Cancer, "Exposure to Artificial UV Radiation and Skin Cancer", (2006), IARC Working Group Reports, vol. 1, (Year: 2006) pp. 61-62.

* cited by examiner

ENHANCED STABILITY OF ZINC PYRITHIONE IN OXIDATIVE ENVIRONMENTS, SUCH AS SCALP SEBACEOUS FLUID

FIELD OF THE INVENTION

The present invention relates to the use of thiol complexes in personal care compositions containing zinc pyrithione to mitigate the loss of beneficial antimicrobial activity due to chemical instability of the zinc pyrithione molecule. Maintaining zinc pyrithione in its biologically active form enables it to control skin surface microbes more effectively, maximizing the resultant benefits, e.g., therapeutic resolution of dandruff and seborrheic dermatitis.

BACKGROUND OF THE INVENTION

For years, and-dandruff shampoos and other personal care produces have been widely used to treat dandruff. In general, anti-dandruff compositions are formulated with anti-dandruff agents in combination with surfactants or conditioning agents in aqueous systems that are intended to deposit the anti-dandruff agents on the scalp. Insoluble particulates such as metal salts of pyrithione are used as anti-dandruff actives because of their efficacy. Zinc pyrithione (ZPT) is the most typical example of such pyrithione salts. It has been observed that the concentration of ZPT is reduced in vivo because of its chemical degradation, which may reduce its biological antimicrobial activity and resultant efficacy. Thus, there still remains a need for improved chemical stability of pyrithione salts and there is a potential to achieve this. The present invention has surprisingly found that the use of thiol complexes of specific chemical structure in personal care compositions that comprise ZPT mitigate the degradation of pyrithione salts and potentially improve the efficacy of the product in terms of its anti-dandruff efficacy.

SUMMARY OF THE INVENTION

The present invention is directed to a personal care composition comprising:
(a) A polyvalent metal salt of pyrithione;
(b) A metal complex selected from the group consisting of:

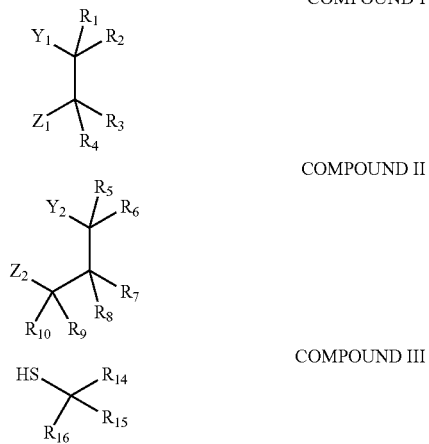

COMPOUND I

COMPOUND II

COMPOUND III wherein $Y_1$, $Y_2$, $Z_1$, $Z_2$ are selected from the following groups: $-NH_2$, $-NHR_{11}$, $-NR_{12}R_{12}$, $-NHCO-R_{20}$, $-SH$, $-OR_{13}$, $-O(C=O)-$, phosphate.

and wherein at least one of $Y_1$ and $Z_1$ of compound I is $-SH$, and wherein at least one of $Y_2$ and $Z_2$ of compound II is $-SH$ $R_1$, $R_2$, $R_3$, $R_4$, $R_5$, $R_6$, $R_7$, $R_8$, $R_9$, $R_{10}$, can independently be H, alkyl, substituted alkyl, phenyl, aryl;

$R_{14}$ is $-NH_2$, $-NHCO-CH_3$, $-NHR_{17}$, or $-NR_{18}R_{18}$ $R_{15}$ is $-COOH$, $-COOR_{19}$ $R_{11}$, $R_{12}$, $R_{13}$ $R_{16}$, $R_{17}$, $R_{18}$, $R_{19}$, $R_{20}$ can be independently be alkyl, substituted alkyl, phenyl, aryl.

and wherein the metal of the complex is selected from the group consisting of zinc, copper, and iron.

DETAILED DESCRIPTION OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

Where amount ranges are given, these are to be understood as being the total amount of said ingredient in the composition, or where more than one species fall within the scope of the ingredient definition, the total amount of all ingredients fitting that definition, in the composition. All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Pyridinethione Salts

Pyridinethione scalp health agent particulates, especially 1-hydroxy-2-pyridinethione salts, are one type of a particulate scalp health agent for use in compositions of the present invention. The concentration of pyridinethione scalp health agent particulate typically ranges from about 0.05% to about 5%, by weight of the composition, further the concentration of scalp health agent ranges from about 0.1% to about 3%, by weight of the composition, or from about 0.1% to about 2%. In another aspect of the present invention, pyridinethione salts include those formed from heavy metals such as zinc, copper, tin, cadmium, magnesium, aluminum and zirconium. The present invention may have a pyridinethione salts formed from a heavy metal zinc, and further may have the zinc salt of 1-hydroxy-2-pyridinethione (known as "zinc pyridinethione" or "ZPT"), and yet further may have 1-hydroxy-2-pyridinethione salts in platelet particle form, wherein the particles have an average size of up to about 20μ. The present invention may have the particles having an average size up to about 5μ, and further up to about 2.5μ. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the scalp health agent particulate in the compositions herein, that the growth or re-growth of hair may be stimulated or regulated, or both, or that hair loss may be reduced or inhibited, or that hair may appear thicker or fuller.

Metal Complex

In the present invention, a metal complex may be selected from the following group:

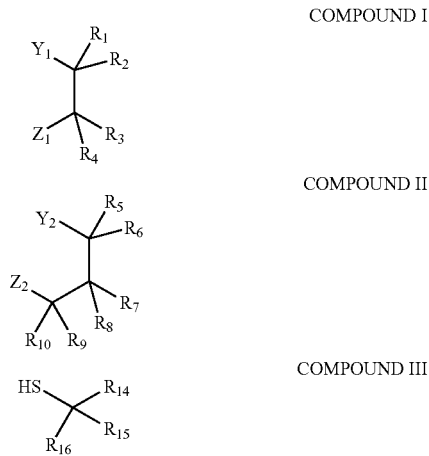

COMPOUND I

COMPOUND II

COMPOUND III wherein $Y_1$, $Y_2$, $Z_1$, $Z_2$ are selected from the following groups: —$NH_2$, —$NHR_{11}$, —$NR_{12}R_{12}$,
—NHCO—$R_{20}$, —SH, —$OR_{13}$, —O(C═O)—, phosphate.

and wherein at least one of $Y_1$ and $Z_1$ of compound I is —SH, and wherein at least one of $Y_2$ and $Z_2$ of compound II is —SH $R_1$, $R_2$, $R_3$, $R_4$, $R_5$, $R_6$, $R_7$, $R_8$, $R_9$, $R_{10}$, can independently be H, alkyl, substituted alkyl, phenyl, aryl;

$R_{14}$ is —$NH_2$, —NHCO—$CH_3$, —$NHR_{17}$, or —$NR_{18}R_{18}$ $R_{15}$ is —COOH, —$COOR_{19}$ $R_{11}$, $R_{12}$, $R_{13}$ $R_{16}$, $R_{17}$, $R_{18}$, $R_{19}$, $R_{20}$ can be independently be alkyl, substituted alkyl, phenyl, aryl.

and wherein the metal of the complex is selected from the group consisting of zinc, copper, and iron. Nonlimiting examples of a metal complex may include the zinc cysteamine complex, zinc L-cysteine complex, zinc cysteine ester and zinc/sodium cysteine complex.

The composition of the present invention may comprise an effective amount of a metal complex. The composition of the present invention may comprise a ratio of a polyvalent metal salt to a metal complex from about 1:10; from about 1:100, or from about 10:1, by total weight of the composition.

Zinc-Containing Layered Material

The composition comprises an effective amount of a zinc-containing layered material. Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. The ZLM may be selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. The ZLM may be a layered double hydroxide conforming to the formula $[M^{2+}_{1-x}M^{3+}_x(OH)_2]^{x+} A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). The ZLM may be a hydroxy double salt conforming to the formula $[M^{2+}_{1-x}M^{2+}_{1+x}(OH)_{3(1-y)}]^+ A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+} 2x\ A^- \cdot nH_2O$. This latter formula represents (where x=0.4) materials such as zinc hydroxychloride and zinc hydroxynitrate. The ZLM may be zinc hydroxychloride and/or zinc hydroxynitrate. These are related to hydrozincite as well wherein a divalent anion replace the monovalent anion. These materials can also be formed in situ in a composition or in or during a production process.

The composition of the present invention may comprise basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

The composition of the present invention may comprise an effective amount of a zinc-containing layered material. The composition of the present invention may comprise from about 0.001% to about 10%, or from about 0.01% to about 7%, or from about 0.1% to about 5% of a zinc-containing layered material, by total weight of the composition.

It has been found that the measured concentration of soluble pyrithione decreases with time in environments akin to scalp sebaceous fluid, such as a mixture of olive oil and oleic acid. As Table 1 shows, when ZPT is placed in the presence of only olive oil the concentration of measured soluble pyrithione remains high over a 96 h exposure time. However, when a fatty acid (oleic acid), like those present in scalp sebaceous fluid is included, only 65% of the soluble pyrithione is retained in the same period (Example 2). Many anti-dandruff formulations include a zinc source in addition to ZPT, such as basic zinc carbonate (ZC). As Example 3 shows, addition of ZC to ZPT in the artificial scalp sebaceous fluid had only a nominal impact on the amount of soluble pyrithione retained after 96 h exposure. Examples 4-6 show perhaps a slight increase in the amount of soluble pyrithione retained versus ZPT+ZC when amino acids are added to ZPT under the same conditions. The result is markedly different in the presence of zinc-complexed cysteamine (Example 7). Inclusion of the zinc cysteamine complex completely counters the impact of the oleic acid and the result matches Example 1.

TABLE 1

| Example | Composition | Soluble Pyrithione Retained after 96 h (%) |
|---|---|---|
| 1 | ZPT in Olive Oil | 99 |
| 2 | ZPT in Olive Oil + Oleic Acid mixture | 65 |
| 3 | ZPT + ZC in Olive Oil + Oleic Acid mixture | 68 |
| 4 | ZPT + cysteamine in Olive Oil + Oleic Acid mixture | 61 |
| 5 | ZPT + L-cysteine in Olive Oil + Oleic Acid mixture | 77 |
| 6 | ZPT + L-methionine in Olive Oil + Oleic Acid mixture | 72 |
| 7 | ZPT + zinc cysteamine complex in Olive Oil + Oleic Acid mixture | 99 |

The positive impact observed in Example 7 with a zinc-thiol complex is further exhibited in time course experiments. As Table 2 shows, after 2 days incubation in artificial scalp sebaceous fluid (olive oil+oleic acid), only the compositions that contained a zinc thiol complex (Examples 14-17) exhibited higher soluble pyrithione concentrations than that taught in the art (Example 10) and this effect is often particularly apparent after 7 days incubation. The combination of ZPT, ZC, and the zinc-thiol complexes would be expected to be particularly advantageous for retention of soluble pyrithione in a sebum-like oxidative environment.

TABLE 2

| Example | Composition | Soluble Pyrithione Retained after 2 days (%) | Soluble Pyrithione Retained after 7 days (%) |
|---|---|---|---|
| 8 | ZPT in Olive Oil | 100 | 100 |
| 9 | ZPT in Olive Oil + Oleic Acid mixture | 64 | 33 |
| 10 | ZPT + ZC in Olive Oil + Oleic Acid mixture | 80 | 40 |
| 11 | ZPT + cysteamine in Olive Oil + Oleic Acid mixture | 45 | 37 |
| 12 | ZPT + L-cysteine in Olive Oil + Oleic Acid mixture | 76 | 44 |
| 13 | ZPT + cysteine ester in Olive Oil + Oleic Acid mixture | 60 | 27 |
| 14 | ZPT + zinc L-cysteine complex in Olive Oil + Oleic Acid mixture | 83 | 44 |
| 15 | ZPT + zinc cysteine ester complex in Olive Oil + Oleic Acid mixture | 83 | 64 |
| 16 | ZPT + zinc/sodium cysteine complex in Olive Oil + Oleic Acid mixture | 97 | 71 |
| 17 | ZPT + ZC + zinc cysteamine complex in Olive Oil + Oleic Acid mixture | 94 | Not run |

Material Sources:
  ZPT: Lonza Group Chemicals
  Olive Oil: Sigma Aldrich, catalogue number 01514
  Oleic Acid: Cremer Group, Cremerac OLS 70 Oleic Kosher
  Zinc Carbonate: Brüggemann Chemical, Zinc Carbonate AC
  Cysteamine: Sigma Aldrich, catalogue number 30070
  L-Cysteine: Sigma Aldrich, catalogue number 168149
  L-Methionine: Sigma Aldrich, catalogue number M9625
Sample Preparation and Analysis:
Synthesis of Zinc Cysteamine Complex To a solution of 2-mercaptoethylamine hydrochloride (cysteamine hydrochloride, 170 g, 1.50 mol) in water (100 ml) under nitrogen is added sodium hydroxide (25% in water, 390 ml, 3.0 mol) within approximately three minutes. Then, while stirring at room temperature, a solution of zinc sulfate heptahydrate (212 g, 737 mmol) in water (270 ml) is added dropwise within 40 min. The resulting suspension is stirred at room temperature for 21 h.

The product is filtered off, washed with water (four times 350 ml) and dried overnight (20 mbar, 55° C.). Zinc cysteamine complex ($Zn(S-CH_2-CH_2-NH_2)_2$, 150 g, 94% yield) is obtained as a colorless solid. Content determination by $^1H$ NMR (d6-DMSO) with an internal standard (sulfolane or triisobutyl phosphate) indicated, that the product had a strength of >95%.

Elemental analysis: calculated: C, 22.07%; H, 5.56%; N, 12.87%; found: C, 21.9%; H, 5.3%; N, 13.1%.

$^1$H NMR (d6-DMSO, 400 MHz): δ 3.42 (t, J=6 Hz, 2H), 2.62 (quint, J=6 Hz, 2H), 2.44 (t, J=6 Hz, 2H).

Synthesis of Zinc L-Cysteine Complex

To a solution of L-cysteine (9.69 g, 80.0 mmol) in water (200 ml) under nitrogen a solution of zinc sulfate heptahydrate (11.5 g, 40.0 mmol) is added at room temperature. To the resulting clear solution aqueous ammonia (25%, 6.0 ml, 80 mmol) is added dropwise while stirring, whereupon a colorless solid precipitated. The suspension is stirred at room temperature for 18 h. The mixture is then heated to 100° C. for one hour, allowed to cool to room temperature, and filtered. The solid is washed with hot water (100 ml), then triturated with hot ethanol (100 ml), filtered, and dried under reduced pressure. Zinc L-cysteine complex (Zn(S—$CH_2$—CH($NH_2$)—$CO_2$), 6.43 g, 87% yield) is obtained as a colorless solid.

Elemental analysis: calculated: C, 19.53%; H, 2.73%; N, 7.59%; found: C, 19.3%; H, 2.9%; N, 7.9%.

$^1$H NMR (d6-DMSO, $D_2O$, DCl, 400 MHz): δ 4.26 (t, J=6 Hz, 3.5H), 3.13 (dd, J=16 Hz, 6 Hz, 1H), 3.00 (dd, J=16 Hz, 6 Hz, 1H).

Synthesis of Zinc L-Cysteine Ethyl Ester Complex

To a solution of L-cysteine ethyl ester hydrochloride (19.0 g, 103 mmol) in water (200 ml) at room temperature under nitrogen is added a solution of zinc sulfate heptahydrate (14.4 g, 50.0 mmol) in water (100 ml). Then aqueous ammonia (25%, 16 ml, 0.21 mmol) is added dropwise while stirring, and the resulting suspension is stirred at room temperature for two hours. The suspension is filtered, and the solid is washed with water (five times with 50 ml) and dried (40° C., 10 mbar) overnight. Zinc L-cysteine ethyl ester complex (Zn(S—$CH_2$—CH($NH_2$)—$CO_2$Et)$_2$, Mwt 361.8 g/mol; 17.2 g, 95% yield) is obtained as a colorless solid.

Elemental analysis: calculated: C, 33.2%; H, 5.57%; N, 7.74%; found: C, 32.2%; H, 5.1%; N, 7.8%.

$^1$H NMR (d6-DMSO, 400 MHz): δ 4.13 (quart, J=7 Hz, 2H), 3.97 (br d, J=5 Hz, 2H), 3.44 (m, 1H), 2.70 (dd, J=16 Hz, 4 Hz, 1H), 2.57 (dd, J=16 Hz, 6 Hz, 1H), 1.22 (t, J=7 Hz, 3H).

Synthesis of Zinc N-Acetyl-L-Cysteine Sesquihydrate Complex

To a suspension of N-acetylcysteine (32.7 g, 200 mmol) in water (103 ml) under nitrogen is added portionwise while stirring zinc carbonate (25.3 g, 202 mmol). The mixture is stirred at room temperature for one hour, filtered over Celite, and the filtrate is kept at room temperature for 20 h. The filtrate is diluted with ethanol (200 ml), mechanically triturated with a spatula, and the suspension is stirred at room temperature for one hour. Filtration and drying (50° C., 10 mbar) yielded zinc N-acetyl-L-cysteine sesquihydrate (Zn(S—$CH_2$—CH(NH—COMe)-$CO_2$)-1.5$H_2O$; Mwt 253.58 g/mol, 39.4 g, 78% yield). Content determination by $^1$H NMR with an internal standard (3-picoline) indicated a strength of 99%.

Elemental analysis: calculated: C, 23.7%; H, 3.98%; N, 5.52%; found: C, 23.6%; H, 3.4%; N, 5.8%.

$^1$H NMR ($D_2O$, 400 MHz): δ 4.28 (t, J=6 Hz, 1H), 2.77 (m, 2H).

Synthesis of Zinc/Sodium L-Cysteine Pentahydrate Complex

To a suspension of L-cysteine (20.1 g, 166 mmol) in water (20.3 ml) at room temperature under nitrogen is added an aqueous solution of sodium hydroxide (2N, 171 ml, 342 mmol). Then a solution of $ZnCl_2$ (11.1 g, 81.4 mmol) in water (18.7 ml) is added. After stirring at room temperature for two hours the solution is filtered, and the filtrate is diluted with ethanol (440 ml). The resulting suspension is stirred at room temperature overnight.

The suspension is filtered, and the solid is washed with cold ethanol (100 ml) and dried under reduced pressure at room temperature for two days. Zinc/sodium L-cystein complex pentahydrate (Zn(S—$CH_2$—CH($NH_2$)—$CO_2Na)_2$-5$H_2O$; Mwt 439.71 g/mol, 30.1 g, 84% yield) is obtained as a colorless solid. Content determination by $^1$H NMR with an internal standard (sulfolane) indicates a strength of 92%.

Elemental analysis: calculated: C, 16.39%; H, 4.58%; N, 6.37%; found: C, 16.1%; H, 4.7%; N, 6.8%.

$^1$H NMR ($D_2O$, 400 MHz): δ 3.41 (dd, J=8 Hz, 4 Hz, 1H), 2.83 (dd, J=13 Hz, 4 Hz, 1H), 2.69 (dd, J=13 Hz, 8 Hz, 1H).

Data shown in Examples 1-17 is generated by following this procedure. First a stock solution of soluble ZPT in olive oil is created. Excess particulate ZPT is combined with olive oil and stirred overnight at RT. For example, 50 mg of ZPT is combined with 40 mL of olive oil in a foil wrapped glass container, then swirled on a waveplate incubator at 34 C for 23 hours. Then all particulate ZPT is pelleted by centrifuging the stock solution, and the quantity of soluble ZPT in the supernatant is measured using the HPLC method subsequently described. This supernatant is referred to as the 'soluble ZPT stock solution' from hereon.

Per Example, a 2.8 g aliquot of the soluble ZPT stock solution is then portioned into clean light-protected glass vial and there combined with the other ingredients described. Each vial is brought to a 4.0 g mass of liquid through addition of either olive oil or oleic acid. Thus, samples containing oleic acid have a 70 to 30 weight ratio of olive oil to oleic acid. Then if any other additive is included it is added at an approximately 10× weight ratio to the soluble ZPT. Samples that now reflected all components listed in the Example compositions are swirled on a waveplate incubator at 34 C for the time indicated, then centrifuged and the supernatant analyzed by HPLC to determine the concentration of soluble pyrithione. In examples 8-17 where multiple timepoints are shown, the reported data is acquired from the same sample, simply sampled for HPLC at multiple increments. The percent of soluble total pyrithione retained is calculated by dividing the value at the appointed timepoint by the initial value.

The concentration of soluble pyrithione is determined via the following procedure. A 0.1 mL aliquot of the supernatant is combined with 0.3 mL of DMSO, then 0.7 mL of a 0.05M EDTA solution with 50 mM added with 50 mM $K_2HPO_4$. A quick vortex to mix, then vortexes at 250 rpm for 20 min. Centrifuge at 13000 rpm for 10 min Carefully pipette 0.6 ml of the bottom solution into 1 ml syringe connected to filter with 60 ul 1% PDS added. Filter into 2 ml sample vial for HPLC analysis.

The samples prepared for analysis above are assessed with an Agilent 1100 HPLC with an autosampler or equivalent, equipped with a UV detector. The column used is an Agilent Poroshell 120 EC-C18 3.0×30 mm, 2.7 micron, P.N. 691975-302. The flowrate is 1.5 mL/min, injection volume: 2 uL, detector wavelength: 236 nm, runtime: 2.5 min, solvent A: 0.1% phosphoric acid, Solvent B: 100% HPLC grade acetonitrile, mobile phase: 80% solvent A and 20% solvent B, column temperature: 50 C and detection sample rate: >10 Hz.

Personal Care Composition Components

2-Pyridinol-N-Oxide Materials

2-Pyridinol-N-oxide materials suitable for use in this invention include a substituted or unsubstituted 2-pyridinol-N-oxide material or a salt thereof. Included within the scope of this invention are tautomers of this material, e.g., 1-hydroxy-2(1H)-pyridinone. The substituted or unsubstituted 2-pyridinol-N-oxide material and its corresponding tautomeric form, 1-hydroxy-2(1H)-pyridinone, are shown below:

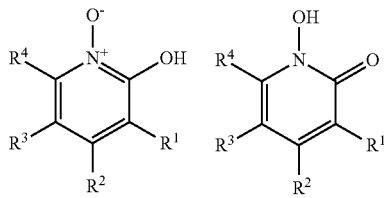

where $R^1$, $R^2$, $R^3$, $R^4$ groups are independently selected from the group consisting of H, Cl, Br, I, F, NO, $NO_2$, and $(CH_2)_nG$, where each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, and $N(R^5R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $^+N(R^7R^8R^9R^{10})$, and $1/q\ M'^{q+}$ where M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

In certain aspects, the 2-pyridinol-N-oxide material is a 2-pyridinol-N-oxide material or tautomer thereof according to the formula(s) above, where $R^1$, $R^2$, $R^3$, $R^4$ are independently selected from the group consisting of H, Cl, and $(CH_2)_nG$, where G is independently selected from the group consisting of $(O)_mSO_3M^3$, $(O)_mCO_2M^3$, $(O)_mC(O)(R^5)$, $(O)_mCN$, and $(O)_m(R^5)$, where m is 0 or 1. In other aspects, the 2-pyridinol-N-oxide material is a 2-pyridinol-N-oxide material according to the formula above, where $R^1$, $R^2$, $R^3$, $R^4$ are independently selected from the group consisting of H, $SO_3M^3$, and $CO_2M^3$. In still other aspects, $R^1$, $R^2$, $R^3$, $R^4$ are independently selected from the group consisting of H, $SO_3M^3$, and $CO_2M^3$, where no more than one R', $R^2$, $R^3$, $R^4$ is $SO_3M^3$ or $CO_2M^3$.

In certain aspects, the 2-pyridinol-N-oxide material is the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, $½ Mg^{2+}$, or $½ Ca^{2+}$, substituted ammonium, such as $C_1$-$C_6$ alkanolammnonium, mono-ethanolamine (MEA), tri-ethanolamine (TEA), di-ethanolamine (DEA), or any mixture thereof. In some aspects, in solution, the cation may be dissociated from the 2-pyridinol-N-oxide or the 1-hydroxy-2(1H)-pyridinone anion.

In certain aspects, the 2-pyridinol-N-oxide material is of a substituted or unsubstituted 2-pyridinol-N-oxide material. Salts for use herein include those formed from the polyvalent metals barium, bismuth, strontium, copper, zinc, cadmium, zirconium and mixtures thereof.

In some aspects, the 2-pyridinol-N-oxide material is selected from the group consisting of: 6-hydroxy-3-pyridinesulfonic acid, 1-oxide (CAS 191672-18-1); 2-hydroxypyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available from, for example, Sigma-Aldrich (St. Louis, Mo.) and/or Aces Pharma (Branford, Conn.).

In certain aspects, the 2-pyridinol-N-oxide material is a 2-pyridinol-N-oxide material selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

In certain aspects, the 2-pyridinol-N-oxide material is a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1, 2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, Mo.), Princeton Building Blocks (Monmouth Junction, N.J.), 3B Scientific Corporation (Libertyville, Ill.), SynFine Research (Richmond Hill, ON), Ryan Scientific, Inc. (Mt. Pleasant, S.C.), and/or Aces Pharma (Branford, Conn.).

In certain aspects, the 2-pyridinol-N-oxide material is a 2-pyridinol-N-oxide material or tautomer thereof according to the formula(s) below:

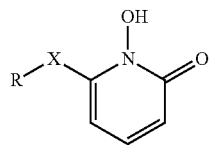

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

In certain aspects, the 2-pyridinol-N-oxide material is a 2-pyridinol-N-oxide material or tautomer thereof according to the formula(s) below:

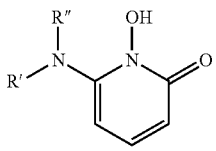

Wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013. In certain aspects, the 2-pyridinol-N-oxide material is 1-Hydroxy-4-methyl-6-(2,4,4-trimethylpentyl)-2-pyridone monoethanolamine salt.

In the present invention, the personal care composition may contain from about 0.1% to about 10% of a substituted or unsubstituted 2-pyridinol N-oxide material. Alternatively, the personal care composition may contain from about 0.3% to about 3% of a substituted or unsubstituted 2-pyridinol N-oxide material. Alternatively, the personal care composition may contain from about 0.5% to about 2% of a substituted or unsubstituted 2-pyridinol N-oxide material.

Detersive Surfactant

The present invention may be present in the form of a shampoo, conditioner, or leave on treatment. The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. The anionic surfactant may be sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Further, zwitterionics such as betaines may be selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

Aqueous Carrier

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

A. Cationic Surfactant System

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system can be included in the composition at a level by weight of from about 0.1% to about 10%, from about 0.5% to about 8%, from about 0.8% to about 5%, and from about 1.0% to about 4%.

Mono-Long Alkyl Quaternized Ammonium Salt

The monoalkyl quaternized ammonium salt cationic surfactants useful herein are those having one long alkyl chain which has about 22 carbon atoms and may be a C22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

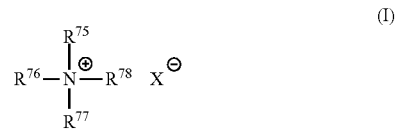

wherein one of $R^{75}$, $R^{76}$, $R^{77}$ and $R^{78}$ is selected from an alkyl group of 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of about 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of about 22 carbons. Exemplary tertiary amido amines include: behenamidopropyldimethylamine, behenamidopropyldiethylamine, behenamidoethyldiethylamine, behenamidoethyldimethylamin. Useful amines in the present invention are disclosed in U.S. Pat. No. 4,275,055, Nachtigal, et al. These amines can also be used in combination with acids such as £-glutamic acid, lactic acid, hydrochloric acid, malic acid, succinic acid, acetic acid, fumaric acid, tartaric acid, citric acid, glutamic hydrochloride, maleic acid, and mixtures thereof; further, may be £-glutamic acid, lactic acid, and/or citric acid. The amines herein can be partially neutralized with any of the acids at a molar ratio of the amine to the acid of from about 1:0.3 to about 1:2, and/or from about 1:0.4 to about 1:1.

Di-Long Alkyl Quaternized Ammonium Salt

Di-long alkyl quaternized ammonium salt can be combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of from about 10% to about 50%, and/or from about 30% to about 45%.

The di-long alkyl quaternized ammonium salt cationic surfactants useful herein are those having two long alkyl chains having about 22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

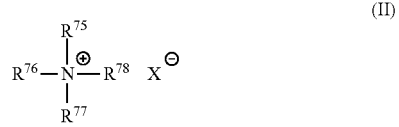

(II)

wherein two of $R^{75}$, $R^{76}$, $R^{77}$ and $R^{78}$ is selected from an alkyl group of from 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of from 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (C22) dimethyl ammonium chloride, ditallow alkyl dimethyl ammonium chloride, dihydrogenated tallow alkyl dimethyl ammonium chloride. Such dialkyl quaternized ammonium salt cationic surfactants also include, for example, asymmetric dialkyl quaternized ammonium salt cationic surfactants.

B. High Melting Point Fatty Compound

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rinsability from the hair when the consumer rinses off the composition.

The high melting point fatty compound can be included in the conditioner composition at a level of from about 0.1% to about 20%, alternatively from about 1% to about 15%, and alternatively from about 1.5% to about 8% by weight of the composition, in view of providing improved conditioning benefits such as slippery feel during the application to wet hair, softness and moisturized feel on dry hair.

C. Aqueous Carrier

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Additional Components

The personal care compositions may include shampoo composition, conditioner compositions, and/or leave-on treatments described herein may optionally comprise one or more additional components known for use in personal care compositions including hair care compositions or personal cleansing care products, provided that the additional components are physically and chemically compatible with the essential components described herein, or do not otherwise unduly impair product stability, aesthetics or performance Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the personal care compositions.

Non-limiting examples of additional components for use in the personal care compositions include conditioning agents, natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins 1. Conditioning Agent The personal care compositions may comprise one or more conditioning agents. Conditioning agents include materials that are used to give a particular conditioning benefit to hair.or skin The conditioning agents useful in the personal care compositions of the present invention typically comprise a water-insoluble, water-dispersible, non-volatile, liquid that forms emulsified, liquid particles. Suitable conditioning agents for use in the personal care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Benefit Agents

The personal care composition may further comprise one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, perfumes, brighteners, enzymes, sensates, attractants, dyes, pigments, bleaches, and mixtures thereof.

The personal care compositions of the present invention may be presented in typical personal care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos, and treatment products; and any other form that may be applied to hair.

The personal care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The personal care composition may be in a single phase or a single product, or the personal care composition may be in a separate phases or separate products. If two products are used, the products may be used together, at the same time or sequentially. Sequential use may occur in a short period of time, such as immediately after the use of one product, or it may occur over a period of hours or days.

Examples

Non-Limiting Examples

The shampoo compositions illustrated in the following examples are prepared by conventional formulation and mixing methods. All exemplified amounts are listed as weight percents on an active basis and exclude minor materials such as diluents, preservatives, color solutions, imagery ingredients, botanicals, and so forth, unless otherwise specified. All percentages are based on weight unless otherwise specified.

| Component | Example | | | | | | | | | |
|---|---|---|---|---|---|---|---|---|---|---|
| | 1 | 2 | 3 | 4 | 5 | 6 | 7 | 8 | 9 | 10 |
| Guar hydroxypropyl-trimonium chloride 1 | 0.3 | 0.3 | 0.3 | 0.25 | 0.3 | 0.3 | 0.3 | 0.3 | 0.3 | 0.3 |
| Acrylamide/ Triquat 2 | — | — | — | — | — | 0.03 | — | — | — | — |
| Sodium laureth-1 sulfate 3 | 12 | 12 | 12.5 | 12 | 12 | 11.5 | 12 | 12 | 12 | 12 |

-continued

| | | | | | | | | | | |
|---|---|---|---|---|---|---|---|---|---|---|
| Sodium Lauryl sulphate 4 | 0 | 0 | — | — | — | 1.5 | — | — | — | — |
| Cocamidopropyl betaine 5 | 1.5 | 1.5 | 1.5 | 1.5 | — | 1.25 | 1.5 | 1.5 | 1.5 | 1.5 |
| Cocamide MEA 6 | 1.5 | 1.5 | 1.5 | 1.5 | 1.5 | 2 | 1.5 | 1.5 | 1.5 | 1.5 |
| Dimethicone 7 | 2.7 | 0.8 | 0.8 | 0.85 | — | 0.8 | 0.8 | 0.8 | 0.8 | 0.8 |
| Dimethiconol 8 | — | — | — | — | 1 | — | — | — | — | — |
| Zinc Pyrithione 9 | 1 | 1 | 1 | 1 | 1 | 1 | 1 | 1 | 1 | 1 |
| Zinc Carbonate 10 | 1.61 | 1.61 | 1.61 | 1.61 | 1.61 | 1.61 | 1.61 | — | — | — |
| Zinc cysteamine complex | 10 | — | — | — | — | — | — | — | — | — |
| L-cysteine ethyl ester complex | — | 10 | — | — | — | — | — | — | — | — |
| Zinc/Sodium L-cysteine pentahydrate complex | — | — | 10 | — | — | — | — | — | — | — |
| Zinc L-cysteine complex | — | — | — | 10 | — | — | — | — | — | — |
| Zinc cysteamine complex | — | — | — | — | 10 | — | — | — | — | — |
| L-cysteine ethyl ester complex | — | — | — | — | — | 10 | — | — | — | — |
| Zinc/Sodium L-cysteine pentahydrate complex | — | — | — | — | — | — | 10 | — | — | — |
| Zinc cysteamine complex | — | — | — | — | — | — | — | 10 | — | — |
| L-cysteine ethyl ester complex | — | — | — | — | — | — | — | — | 10 | — |
| Zinc/Sodium L-cysteine pentahydrate complex | — | — | — | — | — | — | — | — | — | 10 |
| Stearyl Alcohol 11 | — | — | — | — | 1.29 | — | — | — | — | — |
| Cetyl Alcohol 12 | — | — | — | — | 0.71 | — | — | — | — | — |
| Glycol distearate 13 | 1.5 | 1.5 | 1.5 | 1.5 | 1.5 | 1.5 | 1.5 | 1.5 | 1.5 | 1.5 |
| Preservative 14 | 0.05 | 0.05 | 0.05 | 0.05 | 0.05 | 0.05 | 0.05 | 0.05 | 0.05 | 0.05 |
| Piroctone Olamine 15 | — | — | — | — | 1 | 1 | 1 | 1 | — | — |
| Caffeine 16 | 0.1 | 0.1 | 0.1 | 0.1 | 0.1 | — | 0.1 | 0.1 | 0.1 | 0.1 |
| Niacinamide 17 | 0.005 | 0.005 | — | — | 0.005 | — | 0.005 | 0.005 | — | — |
| Panthenol 18 | 0.005 | 0.005 | — | — | 0.005 | — | 0.005 | 0.005 | — | — |
| Polyquaternium-10 19 | 0.2 | 0.1 | 0.2 | 0.1 | 0.1 | — | 0.2 | 0.1 | 0.2 | 0.1 |
| Sodium Xylene Sulfonate 20 | QS | QS | QS | QS | QS | QS | QS | QS | QS | QS |
| Fragrance | 0.9 | 0.9 | 0.9 | 0.9 | 0.9 | 0.8 | 0.9 | 0.9 | 0.9 | 0.9 |
| Hydrochloric Acid 6N | QS | QS | QS | QS | QS | QS | QS | QS | QS | QS |
| Sodium Benzoate | 0.25 | 0.25 | 0.25 | 0.25 | 0.25 | 0.25 | 0.25 | 0.25 | 0.25 | 0.25 |
| Sodium Chloride | QS | QS | QS | QS | QS | QS | QS | QS | QS | QS |
| Water | 66.38 | 68.38 | 67.79 | 68.39 | 66.68 | 66.41 | 65.38 | 63.77 | 71.00 | 71.10 |
| Total | 100 | 100 | 100 | 100 | 100 | 100 | 100 | 100 | 100 | 100 |

1 Jaguar C500 from Solvay with a M. Wt. of about 500,000 g/mol and charge density of about 0.8 meq/g.
2 Polyquaternium-76 (PQ-76) from Rhodia with a M. Wt. of about 1,000,000 g/mol and charge density of about 1.6 meq/g.
3 Sodium laureth-1 sulfate at 26% active from the Stepan Company 4 Sodium Lauryl sulfate at 29% active from the Stepan Company
5 Amphosol HCA at 30% active from the Stepan Company
6 Ninol COMF at 85% active from the Stepan Company
7 Viscasil 330M from Momentive Performance Materials with a viscosity of 330,000 cSt (centistokes) utilizing about an average 30 micron emulsion.
8 BELSIL DM 5500 from Wacker Silicones
9 ZPT from Arch Chemical
10 Zinc carbonate from the Bruggeman Group
11 CO-1895 from Procter & Gamble
12 CO-1695 from Procter & Gamble
13 EGDS from Golschmidt Chemical Company
14 Kathon CG from Akzo Nobel
15 Octopirox from Clairiant
16 BASF Beauty Care Solutions
17 Roche Vitamins Inc
18 DSM Nutritional Products (Ayrshire GB)
19 JR30M available from Dow/Amerchol -
20 Stepanate SXS at 40% from Stepan Product Forms The personal care compositions of the present invention may be presented in typical personal care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos, pre-wash product, co-wash product, and personal cleansing products, and treatment products; and any other form that may be applied to hair or skin.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising
(a) A polyvalent metal salt of pyrithione;
(b) A metal complex selected from the group consisting of:

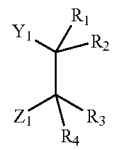

COMPOUND I

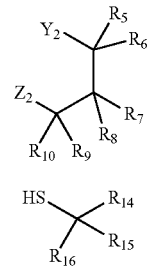

COMPOUND II

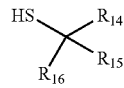

COMPOUND III wherein $Y_1$, $Y_2$, $Z_1$, $Z_2$ are selected from the following groups: $-NH_2$, $-NHR_{11}$, $-NR_{12}R_{12}$, $-NHCO-R_{20}$, $-SH$, $-OR_{13}$, $-O(C=O)-$, phosphate, and wherein at least one of $Y_1$ and $Z_1$ of compound I is $-SH$, and wherein at least one of $Y_2$ and $Z_2$ of compound II is $-SH$ $R_1$, $R_2$, $R_3$, $R_4$, $R_5$, $R_6$, $R_7$, $R_8$, $R_9$, $R_{10}$, can independently be H, alkyl, substituted alkyl, phenyl, aryl;

$R_{14}$ is $-NH_2$, $-NHCO-CH_3$, $-NHR_{17}$, or $-NR_{18}R_{18}$ $R_{15}$ is $-COOH$, $-COOR_{19}$ $R_{11}$, $R_{12}$, $R_{13}$ $R_{16}$, $R_{17}$, $R_{18}$, $R_{19}$, $R_{20}$ can be independently be alkyl, substituted alkyl, phenyl, aryl, and wherein the metal of the complex is selected from the group consisting of zinc, copper and iron and wherein a ratio of the polyvalent metal salt to metal complex is from about 1:10 or from about 1:100 or from about 10:1, by total weight of the composition.

2. A personal care composition comprising
(a) A polyvalent metal salt of pyrithione;
(b) An additional zinc compound; and
(c) A metal complex selected from the group consisting of:

COMPOUND I

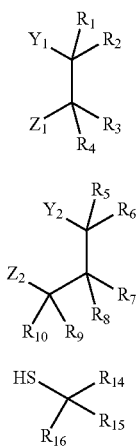

COMPOUND II

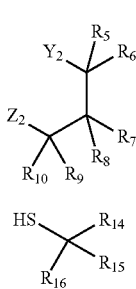

COMPOUND III

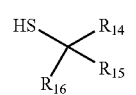

wherein $Y_1$, $Y_2$, $Z_1$, $Z_2$ are selected from the following groups: —$NH_2$, —$NHR_{11}$, —$NR_{12}R_{12}$, —NHCO—$R_{20}$, —SH, —$OR_{13}$, —O(C═O)—, phosphate, and wherein at least one of $Y_1$ and $Z_1$ of compound I is —SH, and wherein at least one of $Y_2$ and $Z_2$ of compound II is —SH $R_1$, $R_2$, $R_3$, $R_4$, $R_5$, $R_6$, $R_7$, $R_8$, $R_9$, $R_{10}$, can independently be H, alkyl, substituted alkyl, phenyl, aryl;

$R_{14}$ is —$NH_2$, —NHCO—$CH_3$, —$NHR_{17}$, or —$NR_{18}R_{18}$ $R_{15}$ is —COOH, —$COOR_{19}$ $R_{11}$, $R_{12}$, $R_{13}$ $R_{16}$, $R_{17}$, $R_{18}$, $R_{19}$, $R_{20}$ can be independently be alkyl, substituted alkyl, phenyl, aryl, and wherein the metal of the complex is selected from the group consisting of zinc, copper and iron and wherein a ratio of the polyvalent metal salt to metal complex is from about 1:10 or from about 1:100 or from about 10:1, by total weight of the composition.

3. A personal care composition according to claim 1 wherein the polyvalent metal salt of pyrithione is from about 0.01% to about 5%, by weight of the composition.

4. A personal care composition according to claim 1 wherein the polyvalent metal salt of pyrithione is from about 0.5% to about 5%, by weight of the composition.

5. A personal care composition according to claim 1 wherein the polyvalent metal salt is zinc pyrithione.

6. A personal care composition according to claim 1 wherein the metal complex is selected from the group consisting of zinc cysteamine complex, zinc L-cysteine complex, zinc cysteine ester, zinc/sodium cysteine complex and mixtures thereof.

7. A personal care composition according to claim 2 wherein the zinc containing layered material is from about 0.01% to about 10%, by weight of the composition.

8. A personal care composition according to claim 7 wherein the zinc containing layered material is from about 0.1% to about 7%, by weight of the composition.

9. A personal care composition according to claim 2 wherein the zinc containing layered material is basic zinc carbonate.

10. A personal care composition according to claim 1 further comprising from about 5% to about 50% of a surfactant.

11. A personal care composition according to claim 10 wherein the surfactant is selected from the group consisting of anionic surfactants, zwitterionic surfactants, amphoteric surfactants, non-ionic surfactants, and mixtures thereof.

12. The personal care composition of claim 1, wherein the personal care composition further comprises one or more additional conditioning agents.

13. The personal care composition of claim 12, wherein said one or more additional conditioning agents is a silicone.

14. The personal care composition of claim 1, wherein the personal care composition further comprises a deposition polymer.

15. The personal care composition of claim 14 wherein the deposition polymer is a cationic polymer.

16. The personal care composition of claim 1, wherein said personal care composition further comprises one or more additional benefit agents.

17. The personal care composition according to claim 16, wherein the one or more additional benefit agents is selected from the group consisting of anti-dandruff agents, anti-fungal agents, anti-itch agents, anti-bacterial agents, anti-microbial agents, moisturization agents, anti-oxidants, vitamins, lipid soluble vitamins, perfumes, brighteners, enzymes, sensates, attractants, dyes, pigments, bleaches, and mixtures thereof.

18. A personal care composition comprising
(c) A polyvalent metal salt of pyrithione;
(d) A metal complex selected from the group consisting of:

COMPOUND I

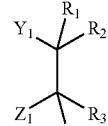

COMPOUND II

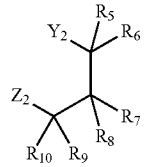

COMPOUND III

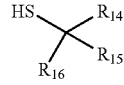

wherein $Y_1$, $Y_2$, $Z_1$, $Z_2$ are selected from the following groups: —$NH_2$, —$NHR_{11}$, —$NR_{12}R_{12}$, —NHCO—$R_{20}$, —SH, —$OR_{13}$, —O(C═O)—, phosphate, and wherein at least one of $Y_1$ and $Z_1$ of compound I is —SH, and wherein at least one of $Y_2$ and $Z_2$ of compound II is —SH $R_1$, $R_2$, $R_3$, $R_4$, $R_5$, $R_6$, $R_7$, $R_8$, $R_9$, $R_{10}$, can independently be H, alkyl, substituted alkyl, phenyl, aryl;

$R_{14}$ is —$NH_2$, —NHCO—$CH_3$, —$NHR_{17}$, or —$NR_{18}R_{18}$ $R_4$, $R_{15}$ can independently be —COOH, —$COOR_{19}$ $R_{11}$, $R_{12}$, $R_{13}$ $R_{16}$, $R_{17}$, $R_{18}$, $R_{19}$, $R_{20}$ can be independently be alkyl, substituted alkyl, phenyl, aryl, and wherein the metal of the complex is selected from the group consisting of zinc, copper and iron and wherein a ratio of the polyvalent metal salt to metal complex is from about 1:10 or from about 1:100 or from about 10:1, by total weight of the composition.

\* \* \* \* \*